(12) United States Patent
Kim (10) Patent No.: US 9,808,499 B2
(45) Date of Patent: Nov. 7, 2017

(54) ORIENTAL MEDICINE COMPOSITIONS MARKED AS SEC 22 AND SEC 33 FOR IMPROVING CHILDREN'S UNDERWEIGHT, LOW GROWTH AND DEPRESSED RESPIRATORY ORGAN

(71) Applicant: Kijoon Kim, Seoul (KR)

(72) Inventor: Kijoon Kim, Seoul (KR)

( * ) Notice: Subject to any disclaimer, the term of this patent is extended or adjusted under 35 U.S.C. 154(b) by 214 days.

(21) Appl. No.: 14/547,353

(22) Filed: Nov. 19, 2014

(65) Prior Publication Data
US 2015/0140115 A1      May 21, 2015

(30) Foreign Application Priority Data

Nov. 19, 2013   (KR) .................. 10-2013-0140934

(51) Int. Cl.
| | | |
|---|---|---|
| A61K 35/32 | (2015.01) | |
| A61K 36/185 | (2006.01) | |
| A61K 36/73 | (2006.01) | |
| A61K 36/75 | (2006.01) | |
| A61K 36/906 | (2006.01) | |
| A61K 36/9068 | (2006.01) | |
| A61K 36/72 | (2006.01) | |
| A61K 36/28 | (2006.01) | |
| A61K 36/42 | (2006.01) | |
| A61K 36/481 | (2006.01) | |
| A61K 36/534 | (2006.01) | |
| A61K 36/538 | (2006.01) | |
| A61K 36/734 | (2006.01) | |
| A61K 36/752 | (2006.01) | |
| A61K 36/8998 | (2006.01) | |
| A61K 36/9064 | (2006.01) | |
| A61K 36/284 | (2006.01) | |
| A61K 36/725 | (2006.01) | |

(52) U.S. Cl.
CPC .......... *A61K 36/9068* (2013.01); *A61K 35/32* (2013.01); *A61K 36/185* (2013.01); *A61K 36/28* (2013.01); *A61K 36/284* (2013.01); *A61K 36/42* (2013.01); *A61K 36/481* (2013.01); *A61K 36/534* (2013.01); *A61K 36/538* (2013.01); *A61K 36/725* (2013.01); *A61K 36/734* (2013.01); *A61K 36/752* (2013.01); *A61K 36/8998* (2013.01); *A61K 36/9064* (2013.01); *A61K 2236/00* (2013.01)

(58) Field of Classification Search
None
See application file for complete search history.

(56) References Cited

U.S. PATENT DOCUMENTS

| | | | | |
|---|---|---|---|---|
| 7,198,804 | B2 * | 4/2007 | Cho | A61K 36/07 424/725 |
| 9,320,772 | B2 * | 4/2016 | Doron | A61K 36/725 |
| 2006/0018867 | A1 * | 1/2006 | Kawasaki | A61K 8/898 424/70.122 |
| 2009/0104295 | A1 * | 4/2009 | Kohno | A23L 33/105 424/757 |
| 2011/0052731 | A1 * | 3/2011 | Park | A61K 36/185 424/728 |

OTHER PUBLICATIONS

Mohammad Najmul Ghani Khan Khazaain-al-Advia, vol. II, 5(pg. No. 04-08) ( Ref. pg. no of publication:375 ) 1911, Nadeem Yunus Printer / Sheikh Mohd Basheer & Sons Lahore, India.†
Mohammad Najmul Ghani Khan Khazaain-al-Advia, vol. II, 9(pg. No. 09-17) ( Ref. pg. no of publication:933-935 ) 1911, Nadeem Yunus Printer / Sheikh Mohd Basheer & Sons Lahore, India.†
Pradumnacharya Vaidya Nilangekar Rasa Yoga Shataka 6(pg. No. 18-23) ( Reg.pg. no of publication:27 ) 1965 Pradumnacharya Vaidya Hydrabad, India.†

* cited by examiner
† cited by third party

*Primary Examiner* — Chris R Tate
*Assistant Examiner* — Randall Winston
(74) *Attorney, Agent, or Firm* — Saliwanchik, Lloyd & Eisenschenk (57) ABSTRACT

The present invention relates to oriental medicine compositions marked as SEC 22 and SEC 33 for improving digestive functions and respiratory functions for improving children's underweight, low growth and depressed respiratory organ, an oriental medicine derived therefrom, and methods of preparing them. According to an example of the present invention, the oriental medicine composition containing broiled fruit of *Crataegus pinnatifida*, broiled root of *Atractylodes japonica*, dried peel of *Citrus unshiu*, broiled sprout of *Hordeum vulgare*, broiled fruit of *Amomum xanthioides*, root of *Zingiber officinale*, dried fruit of *Zizyphi*, and horn of *Cervus elaphus*.

15 Claims, 3 Drawing Sheets

FIG. 5

ORIENTAL MEDICINE COMPOSITIONS MARKED AS SEC 22 AND SEC 33 FOR IMPROVING CHILDREN'S UNDERWEIGHT, LOW GROWTH AND DEPRESSED RESPIRATORY ORGAN

CROSS-REFERENCE TO RELATED APPLICATION

This application claims priority of Korean Patent Application No. 10-2013-0140934, filed on Nov. 19, 2013, in the KIPO (Korean Intellectual Property Office), the disclosure of which is incorporated herein entirely by reference.

BACKGROUND OF THE INVENTION

Field of the Invention

The present invention relates to an oriental medicine composition, and more particularly, oriental medicine compositions marked as SEC 22 and SEC 33 for improving digestive functions and respiratory functions for improving children's underweight, low growth and depressed respiratory organ, an oriental medicine derived therefrom, and methods of preparing them.

Description of the Related Art

Childhood is a stage that one's diet is significantly changed by quitting baby food, where growths based on dietary intakes may significantly vary from one person to another. Furthermore, childhood is a state in which not only muscles and bones, but also various nervous systems including the brain grow and develop, where required amounts of energy and nutrition grow significantly due to increased amount of action. However, although obesity is one from among major social interests, interests on skinny proportion and underweight decrease as one's socioeconomic status is improved. Deficiency of nutrition is still a serious nutritional problem in childhood.

Generally, an underweight is defined to be less than body mass index (BMI) percentage 5 percent (WHO Expert Committee 1996, Kuczmarski et al. 2000. However, parents of children with skinny proportions are highly interested in weight changes of their children, although parents of children are not underweight children.

Conventional researches regarding underweight generally focus on malnutrition based on famine or underweight based on anorexia nervosa. Therefore, even though skinny children without no clinical abnormalities may get health problems due to insufficient dietary intakes, those children may not get medical assistance due to lack of related researches.

Skinny proportions may mean insufficient dietary intakes. Such insufficiency of dietary intakes does not cause growth problems in the short term. However, if insufficiency of dietary intakes persists in the long term, it may inhibit revelation of growth potential. Furthermore, children who do not eat enough, do not eat balanced meals, or refuse new food may be easily led to insufficiency of dietary intakes.

In terms of oriental medicine, children with lack of appetite or underweight are diagnosed as stomach weakness and oriental medicines for treating digestive system are used. Stomach is the organ that controls digestion. If stomach is weak, problem occurs to digest food coming into the body. Therefore, a child feels bloated, thereby reducing appetite and causing underweight. The reason thereof may be inborn stomach weakness or acquired stomach underdevelopment.

SUMMARY OF THE INVENTION

Embodiments of the present invention include oriental medicine compositions for increasing amounts of food eaten by children with lack of appetite by improving digestive functions.

Embodiments of the present invention also include oriental medicine composition for promoting growth of children with skinny proportions and improving underweight by improving not only digestive functions, but also respiratory functions and oriental medicine extracts prepared using the same.

According to an aspect of the present invention, there may be provided an oriental medicine composition for improving digestive functions and respiratory functions, the oriental medicine composition containing broiled fruit of *Crataegus pinnatifida*, broiled root of *Atractylodes japonica*, dried peel of *Citrus unshiu*, broiled sprout of *Hordeum vulgare*, broiled fruit of *Amomum xanthioides*, root of *Zingiber officinale*, dried fruit of *Zizyphi*, and horn of *Cervus elaphus*.

The oriental medicine composition may contain from about 22 weight % to about 26 weight % of the broiled fruit of *Crataegus pinnatifida*, from about 17 weight % to about 21 weight % of the broiled root of *Atractylodes japonica*, from about 12 weight % to about 16 weight % of the dried peel of *Citrus unshiu*, from about 12 weight % to about 16 weight % of the broiled sprout of *Hordeum vulgare*, from about 7 weight % to about 11 weight % of the broiled fruit of *Amomum xanthioides* from about 5 weight % to about 9 weight % of the root of *Zingiber officinale*, from about 5 weight % to about 9 weight % of the dried fruit of *Zizyphi*, and from about 1 weight % to about 5 weight % of the horn of *Cervus elaphus*, with respect to the overall weight of the oriental medicine composition.

The oriental medicine composition may further contain at least one from among fructose; sugars including unrefined sugar, refined sugar, turbinado, and dark brown sugar; natural sweeteners; synthetic sweeteners; maltitol syrup; polyglycitol syrup; palatinos; and oligosaccharides including malto-oligosaccharide, isomalto-oligosaccharide, and fracto-oligosaccharide, wherein the fructose may be crystalline fructose or high fructose corn syrup.

The natural sweeteners may include at least one from among xylitol, erythritol, enzymatically modified stevia glucosyl stevia, stevioside, tomatine, thaumatin, thaumatin, monellin, glycyrrhizin, honey, Maple syrup, Agave syrup, and coconut sugar. The synthetic sweeteners may include at least one or more from among Aspartame, saccharin, acesulfame potassium, and Sucralose. The broiled fruit of *Crataegus pinnatifida* may be fruit of the hawthorn.

According to another aspect of the present invention, there may be provided an oriental medicine composition for improving digestive functions and respiratory functions, the oriental medicine composition containing from about 13 weight % to about 17 weight % of *Ulmi Cortex*, from about 10 weight % to about 15 weight % of broiled fruit of *Crataegus pinnatifida*, from about 8 weight % to about 12 weight % of broiled root of *Atractylodes japonica*, from about 8 weight % to about 12 weight % of *Lufa cylindrica*, from about 8 weight % to about 12 weight % of *Menthae Herba*, from about 5 weight % to about 10 weight % of *Schizonepetae Spica*, from about 5 weight % to about 10 weight % of dried peel of *Citrus unshiu*, from about 5 weight % to about 10 weight % of broiled sprout of *Hordeum vulgare*, from about 3 weight % to about 7 weight % of broiled fruit of *Amomum xanthioides*, from about 3 weight % to about 7 weight % of *Astragali Radix*, from about 1 weight % to about 5 weight % of root of *Zingiber officinale*, from about 1 weight % to about 5 weight % of dried fruit of *Zizyphi*, and from about 0.5 weight % to about 3 weight % of horn of *Cervus elaphus*, with respect to the overall weight of the oriental medicine composition.

The oriental medicine composition may further contain at least one from among fructose including crystalline fructose and high fructose corn syrup; sugars including unrefined sugar, refined sugar, turbinado, and dark brown sugar; natural sweeteners including xylitol, erythritol, enzymatically modified stevia glucosyl stevia, stevioside, tomatine, thaumatin, thaumatin, monellin, glycyrrhizin, honey, Maple syrup, Agave syrup, and coconut sugar; synthetic sweeteners including Aspartame, saccharin, acesulfame potassium, and Sucralose; maltitol syrup; polyglycitol syrup; palatinos; and oligosaccharides including malto-olygosaccharide, isomalto-olygosaccharide, and fracto-olygosaccharide.

According to another aspect of the present invention, there may be provided a method of preparing an oriental medicine extract for improving digestive functions and respiratory functions, the method including preparing an oriental medicine composition containing from about 22 weight % to about 26 weight % of the broiled fruit of *Crataegus pinnatifida*, from about 17 weight % to about 21 weight % of the broiled root of *Atractylodes japonica*, from about 12 weight % to about 16 weight % of the dried peel of *Citrus unshiu*, from about 12 weight % to about 16 weight % of the broiled sprout of *Hordeum vulgare*, from about 7 weight % to about 11 weight % of the broiled fruit of *Amomum xanthioides* from about 5 weight % to about 9 weight % of the root of *Zingiber officinale*, from about 5 weight % to about 9 weight % of the dried fruit of *Zizyphi*, and from about 1 weight % to about 5 weight % of the horn of *Cervus elaphus*; putting the oriental medicine composition in a non-woven fabric bag, putting the non-woven fabric bag in a clay port accommodating water, and preparing the oriental medicine extract by decocting the oriental medicine composition; and filtering the oriental medicine extract.

The method may further include, after the filtering of the oriental medicine extract, adding at least one from among fructose; sugars including unrefined sugar, refined sugar, turbinado, and dark brown sugar; natural sweeteners; synthetic sweeteners; maltitol syrup; polyglycitol syrup; palatinos; and oligosaccharides including malto-olygosaccharide, isomalto-olygosaccharide, and fracto-olygosaccharide to the filtered oriental medicine extract.

Furthermore, the method may further include, after the filtering of the oriental medicine extract, depressurization-condensing the filtered oriental medicine extract. Furthermore, the method may further include, after all of the above-stated operations, drying the oriental medicine extract and preparing the dried oriental medicine extract in the form of powders.

BRIEF DESCRIPTION OF THE DRAWINGS

The above and other features and advantages will become more apparent to those of ordinary skill in the art by describing in detail exemplary embodiments with reference to the attached drawings, in which.

In the following description, the same or similar elements are labeled with the same or similar reference numbers.

DETAILED DESCRIPTION

The present invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes", "comprises" and/or "comprising," when used in this specification, specify the presence of stated features, integers, steps, operations, elements, and/or components, but do not preclude the presence or addition of one or more other features, integers, steps, operations, elements, components, and/or groups thereof. In addition, a term such as a "unit", a "portion", a "module", a "block" or like, when used in the specification, represents a unit that processes at least one function or operation, and the unit or the like may be implemented by hardware or software or a combination of hardware and software.

In the present specification, although terms such as first, second, etc., are used to describe various members, components, areas, layers and/or portions thereof, these members, components, areas, layers and/or portions thereof are not limited to these terms. These terms are used only to distinguish one member, component, area, layer or a portion thereof from another member, component, area, layer or a portion thereof. Accordingly, a first member, a first component, a first area, a first layer, or a portion thereof to be described below may indicate a second member, a second component, a second area, a second layer, or a portion thereof without the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Preferred embodiments will now be described more fully hereinafter with reference to the accompanying drawings.

However, they may be embodied in different forms and should not be construed as limited to the embodiments set forth herein. Rather, these embodiments are provided so that this disclosure will be thorough and complete, and will fully convey the scope of the disclosure to those skilled in the art.

Oriental medicine compositions for improving digestive functions and respiratory functions according to the present invention may include broiled fruit of *Crataegus pinnatifida*, broiled root of *Atractylodes japonica*, dried peel of *Citrus unshiu*, broiled sprout of *Hordeum vulgare*, broiled fruit of *Amomum xanthioides*, root of *Zingiber officinale*, dried fruit of *Zizyphi*, and horn of *Cervus elaphus*. Furthermore, the oriental medicine extracts may further include *Ulmi* Cortex, Lufa *Cylindrica, Menthae Herba, Schizonepetae Spica*, and *Astragali Radix*.

The broiled fruit of *Crataegus pinnatifida* is ripe fruit of a hawthorn in the Rosaceae, promotes digestion by warming stomach, and may be used for stomachache, nausea, diarrhea, hyperacid, chronic enteritis. Furthermore, the broiled fruit of *Crataegus pinnatifida* helps blood flow, eliminates extravasated blood, and has medical effects including cardiotonic effect, blood circulation improving effect, and hypotensive function.

The broiled root of *Atractylodes japonica* is a rhizome of *Atractylodes japonica*, which is a perennial herb in the Asteraceae. The broiled root of *Atractylodes japonica* strengthens stomach and promotes digestion, thus being very effective for chronic indigestion, enteritis, diarrhea and for appetite promotion. Particularly, the broiled root of *Atractylodes japonica* is effective for convalescent people with lack of appetite, general prostration, and excessive sweating. Furthermore, the broiled root of *Atractylodes japonica* also has diuretic effect, thus being widely used for patients with edema due to nephritis or pregnant having edema.

The dried peel of *Citrus unshiu* is peel of ripe fruit of tangerine in the Rutaceae or closely related congeneric plants and is known as a medicinal ingredient having warming property. The dried peel of *Citrus unshiu* relieves clogged energy of body and strengthens function of spleen, thereby curing tympanites, burp, nausea, indigestion, and soft stools, relieves chronic cough and phlegm, and has diuretic effect.

The broiled sprout of *Hordeum vulgare* is sprout of unhulled barley. The broiled sprout of *Hordeum vulgare* has warming property, is effective for digestive problems based on stomach weakness, and is particularly used for indigestion regarding foods made with white flour. Furthermore, the broiled sprout of *Hordeum vulgare* is effective for hypogalactia and has medicinal effects including promoting digestion and decreasing blood pressure.

The broiled fruit of *Amomum xanthioides* is a medicinal ingredient made of fruit of *Amomum villosum* Loureiro, which is a perennial herb in the Zingiberaceae, and is effective for people with problems in Qi flow, lack of appetites, and abdominal inflation with pain. Furthermore, the broiled fruit of *Amomum xanthioides* is used for indigestion and nausea based on gastrointestinal disturbances and is highly effective for symptoms including cold lower abdomen and dysenteric diarrhea.

The root of *Zingiber officinale* is a perennial plant of zingiberaceae of Zingibarales, where root is edible and medicinal. In the oriental medicine, dried rhizome thereof is used as a medicinal herb, which cures chill, fever, nausea, chronic cough, and phlegm based on cold, is effective for stomachache and diarrhea based on food poisoning, and has medicinal effects including triggering secretion of gastric juice, improves digestion, cardio excitation, blood circulation promotion, and microbe inhibition.

The dried fruit of *Zizyphi* is dried ripe jujube having sweet flavor and warming property and being highly effective for vital energy invigoration of a pregnant woman, pains due to cold and weak stomach, loss of appetite, ennui, weakness, nausea based on weak stomach, and nausea based on loss of appetite. The horn of *Cervus elaphus* is horn of a deer dried in the shade, has warming property, and works on the kidneys, the liver, and the heart, thereby being effective for sperm production promotion, blood replenishment, virility promotion, and muscle and bone strengthenment The *Ulmi Cortex* is the bark of a tree obtained by peeling the cork layer of the Bigfruit Elm (*Ulmus macrocarpa* Hance) of Ulmaceae, is highly effective for healing an wound, removes dampness, makes a swelling subside, and soothes pain. The Luffae Fructus Retinervus is a plant of cucurbitaceae, where fluid from the stem improves cough, phlegm, and asthma, cures diabetes, and enhances rhinitis.

The *Menthae Herba* is a perennial plant of Lamiceae and is also known as 'Yasikhyang,' 'Bunhachae,' 'Indancho,' and 'Gubakha' in Korea. There are oil glands secreting peppermint oil on surfaces of leaves, where most of essential oil is stored in the oil glands. The major ingredient of the peppermint oil is menthol, which is used in ointments, pain relievers, stimulants, digestives, and anthelmintics or is used as a refresher or a flavor in products including toothpastes, jams, candies, cosmetics, cigarettes, etc.

Furthermore, the *Schizonepetae Spica* is an annual herbaceous plant of Lamiaceae, is used for perspiration and fever removal at the early stage of a cold, is used for sore throat, skin problems, and stroke, and is effective for stopping blood. The *Astragali Radix* is a perennial herbaceous plant of the pulse family, where root is used as a medicinal herb. The *Astragali Radix* is highly effective for a person who gets easily tired, is weak, and sweats a lot, improves stamina, and improves muscle tension of the whole body.

An oriental medicine composition prepared according to a first embodiment of the present invention contains the broiled fruit of *Crataegus pinnatifida*, the broiled root of *Atractylodes japonica*, the dried peel of *Citrus unshiu*, the broiled sprout of *Hordeum vulgare*, the broiled fruit of *Amomum xanthioides*, the root of *Zingiber officinale*, the dried fruit of *Zizyphi*, and the horn of *Cervus elaphus*, and preferably, contains from about 22 weight % to about 26 weight % of the broiled fruit of *Crataegus pinnatifida*, from about 17 weight % to about 21 weight % of the broiled root of *Atractylodes japonica*, from about 12 weight % to about 16 weight % of the dried peel of *Citrus unshiu*, from about 12 weight % to about 16 weight % of the broiled sprout of *Hordeum vulgare*, from about 7 weight % to about 11 weight % of the broiled fruit of *Amomum xanthioides* from about 5 weight % to about 9 weight % of the root of *Zingiber officinale*, from about 5 weight % to about 9 weight % of the dried fruit of *Zizyphi*, and from about 1 weight % to about 5 weight % of the horn of *Cervus elaphus*. The broiled fruit of *Crataegus pinnatifida*, the broiled root of *Atractylodes japonica*, the dried peel of *Citrus unshiu*, the broiled sprout of *Hordeum vulgare*, the broiled fruit of *Amomum xanthioides*, the root of *Zingiber officinale*, the dried fruit of *Zizyphi*, and the horn of *Cervus elaphus* may all be general dried medicinal herbs used for concocting herbal medicines, where the dried medicinal herbs are prepared using medicinal herbs defined in the "Korea Pharmacopoeia." Furthermore, left-type medicinal herbs may be prepared as thin slices.

If the oriental medicine composition according to the first embodiment of the present invention contains less than 22 weight % of the broiled fruit of *Crataegus pinnatifida* with respect to the overall weight, medicinal effect of the broiled fruit of *Crataegus pinnatifida* is insignificant. Meanwhile, if the oriental medicine composition according to the first embodiment of the present invention contains more than 26 weight % of the broiled fruit of *Crataegus pinnatifida* with respect to the overall weight, indigestion may occur.

Furthermore, if the oriental medicine composition contains less than 17 weight % of the broiled root of *Atractylodes japonica*, medicinal effect of the broiled root of *Atractylodes japonica* is insignificant. Meanwhile, if the oriental medicine composition according to the first embodiment of the present invention contains more than 21 weight % of the broiled root of *Atractylodes japonica*, anti-diarrheal effect is strengthened, thereby causing indigestion and constipation. If the oriental medicine composition according to the first embodiment of the present invention contains less than 12 weight % of the dried peel of *Citrus unshiu*, it is difficult to control water metabolism via body's metabolism and the effect of balancing function of the middle-energizer, which is located between the heart and the belly and manages digesting process is deteriorated. On the other hand, if the oriental medicine composition according to the first embodiment of the present invention contains more than 16 weight % of the dried peel of *Citrus unshiu*, the medicinal effect of the dried peel of *Citrus unshiu* may be inclined to helping movement of energy of body and healing phelgm or asthma, rather than healing tympanites and indigestion by strengthening the spleen.

Furthermore, if the oriental medicine composition according to the first embodiment of the present invention contains less than 12 weight % of the broiled sprout of *Hordeum vulgare*, medicinal effect of the broiled sprout of *Hordeum vulgare* may be insignificant. Meanwhile, if the oriental medicine composition according to the first embodiment of the present invention contains more than 26 weight % of the broiled sprout of *Hordeum vulgare*, indigestion may occur. If the oriental medicine composition according to the first embodiment of the present invention contains less than 7 weight % of the broiled fruit of *Amomum xanthioides*, the broiled fruit of *Amomum xanthioides* is not effective for healing Gastrointestitnal disturbances. Meanwhile, if the oriental medicine composition according to the first embodiment of the present invention contains more than 11 weight % of the broiled fruit of *Amomum xanthioides*, the broiled fruit of *Amomum xanthioides* is not very effective for resolving indigestion.

If the oriental medicine composition according to the first embodiment of the present invention contains less than 5 weight % of the root of *Zingiber officinale*, the root of *Zingiber officinale* is not medicinally effective for triggering secretion of gastric juice and microbe inhibition. Meanwhile, if the oriental medicine composition according to the first embodiment of the present invention contains more than 9 weight % of the root of *Zingiber officinale*, biting taste becomes strong, thereby causing difficulties of taking the oriental medicine composition. Furthermore, if the oriental medicine composition according to the first embodiment of the present invention contains less than 5 weight % of the dried fruit of *Zizyphi*, the dried fruit of *Zizyphi* is not medicinally effective for healing loss of appetite, weakness, nausea, and vomiting due to its warming property. Even if the oriental medicine composition according to the first embodiment of the present invention contains more than 9 weight % of the dried fruit of *Zizyphi*, medicinal effect thereof is not significantly different from that in the case where the oriental medicine composition according to the first embodiment of the present invention contains less than 9 weight % of the dried fruit of *Zizyphi*.

Furthermore, the horn of *Cervus elaphus* is an expensive medicine, where medicinal effects for sperm production promotion, blood replenishment, virility promotion, and muscle and bone strengthenment of a case in which the oriental medicine composition according to the first embodiment of the present invention contains less than 5 weight % of the horn of *Cervus elaphus* are not significantly different from those of a case in which the oriental medicine composition according to the first embodiment of the present invention contains more than 5 weight % of the horn of *Cervus elaphus*. Therefore, the oriental medicine composition according to an embodiment of the present invention may contain from about 1 weight % to about 5 weight % of the horn of *Cervus elaphus*.

The oriental medicine composition according to the present invention having the above-stated composition ratio has not only general medicinal effects of the medicinal herbs contained in the oriental medicine composition, such as strengthening the digestive system against indigestion, constipation, and gastrointestinal disturbances, but also strengthens immune system by increasing weight of an underweighted child by resolving loss of appetite. Weight increase of an underweighted child strengthens immune system, improves stamina, and promotes growth, thus being an important factor for improving health of an underweighted child.

As described above, resolving loss of appetite is led to increasing weight, strengthening immune system, improving stamina, and promoting growth of an underweighted child, thereby significantly improving health of an underweighted child. Therefore, the oriental medicine composition according to the first embodiment of the present invention contains medicinal herbs generally having effects for improving digestive troubles, such as indigestion, constipation, and gastrointestinal disturbances, or strengthening digestive systems based on the weight % as described above, which exhibits excellent effect for resolving loss of appetite of a child.

Furthermore, according to the second embodiment of the present invention, an oriental medicine composition may contain *Ulmi Cortex*, broiled fruit of *Crataegus pinnatifida*, broiled root of *Atractylodes japonica*, *Lufa cylidrica*, *Menthae Herba*, *Schizonepetae Spica*, dried peel of *Citrus unshiu*, broiled sprout of *Hordeum vulgare*, broiled fruit of *Amomum xanthioides*, *Astragali Radix*, root of *Zingiber officinale*, dried fruit of *Zizyphi*, and horn of *Cervus elaphus*, and preferably, may contain from about 13 weight % to about 17 weight % of the *Ulmi Cortex*, from about 10 weight % to about 15 weight % of the broiled fruit of *Crataegus pinnatifida*, from about 8 weight % to about 12 weight % of the broiled root of *Atractylodes japonica*, from about 8 weight % to about 12 weight % of the *Lufa cylidrica*, from about 8 weight % to about 12 weight % of the *Menthae Herba*, from about 5 weight % to about 10 weight % of the *Schizonepetae Spica*, from about 5 weight % to about 10 weight % of the dried peel of *Citrus unshiu*, from about 5 weight % to about 10 weight % of the broiled sprout of *Hordeum vulgare*, from about 3 weight % to about 7 weight % of the broiled fruit of *Amomum xanthioides*, from about 3 weight % to about 7 weight % of the *Astragali Radix*, from about 1 weight % to about 5 weight % of the root of *Zingiber officinale*, from about 1 weight % to about 5 weight % of the dried fruit of *Zizyphi*, and from about 0.5 weight % to about 3 weight % of the horn of *Cervus elaphus*, with respect to the overall weight. The broiled fruit of *Crataegus pinnatifida*, the broiled root of *Atractylodes japonica*, the *Lufa cylidrica*, the *Menthae Herba*, the *Schizonepetae Spica*, the dried peel of *Citrus unshiu*, the broiled sprout of *Hordeum vulgare*, the broiled fruit of *Amomum xanthioides*, the *Astragali Radix*, the root of *Zingiber officinale*, the dried fruit of *Zizyphi*, and the horn of *Cervus elaphus* may all be general dried medicinal herbs used for concocting herbal medicines, where the dried medicinal herbs are prepared using medicinal herbs defined in the "Korea Pharmacopoeia." Furthermore, left-type medicinal herbs may be prepared as thin slices.

If the oriental medicine composition according to the second embodiment of the present invention contains less than 13 weight % of the *Ulmi Cortex*, the effect of the *Ulmi Cortex* for resolving indigestion, such as diarrhea, by removing dampness is insignificant. Meanwhile, if the oriental medicine composition according to the second embodiment of the present invention contains more than 17 weight % of the *Ulmi Cortex*, sleeping effect of the *Ulmi Cortex* may be improved, whereas the effect of the *Ulmi Cortex* for improving of bronchial diseases may become insignificant. If the oriental medicine composition according to the second embodiment of the present invention contains less than 8 weight % of the *Menthae Herba*, the *Menthae Herba* is not medicinally effective. Meanwhile, if the oriental medicine composition according to the second embodiment of the present invention contains more than 12 weight % of the *Menthae Herba*, a medicine taker may be repulsed.

Furthermore, if content of the *Lufa cylidrica* in the oriental medicine composition according to the second embodiment of the present invention is out of a range between about 8 weight % and about 12 weight %, effect of the *Lufa cylidrica* may be insignificant for bronchial diseases, such as coughs, phlegm, and asthma. If content of the *Schizonepetae Spica* in the oriental medicine composition according to the second embodiment of the present invention is out of a range between about 5 weight % and about 10 weight %, the *Schizonepetae Spica* is not medicinally effective for perspiration and stopping blood. If content of the *Astragali Radix* in the oriental medicine composition according to the second embodiment of the present invention is out of a range between about 3 weight % and about 7 weight %, the *Astragali Radix* may be hardly effective for stamina improvement.

The oriental medicine composition according to the present invention having the above-stated composition ratio has not only general medicinal effects of the medicinal herbs contained in the oriental medicine composition, such as strengthening the digestive system against indigestion, constipation, and gastrointestinal disturbances, but also strengthens immune system by increasing weight of an underweighted child by resolving loss of appetite. Weight increase of an underweighted child strengthens immune system, improves stamina, and promotes growth, thus being an important factor for improving health of an underweighted child.

Furthermore, the oriental medicine composition not only strengthens digestive system, but also improves bronchial diseases, such as rhinitis, asthma, allergic reactions, bronchitis, and coughs, thereby resolving loss of appetite of an underweighted child. Various bronchial diseases widely occur at children. When a bronchial disease occurs at a child, the child loses appetite due to symptoms including coughs, phlegm, high fever, and runny nose, and thus energy intake is significantly reduced.

Oriental medicine compositions according to embodiments of the present invention may contain general dried medicinal herbs and may be prepared as powders by crushing the dried medicinal herbs. According to some embodiments of the present invention, An oriental medicine composition according to the present invention may be obtained as a hot water extraction material via a general hot water extraction process, where the hot water extraction material may be prepared to dry extraction powders by lyophilizing the hot water extraction material. Furthermore, according to embodiments of the present invention, the oriental medicine composition may be prepared in any of various forms as long as the oriental medicine composition is prepared based on the above-stated composition ratio, e.g., the oriental medicine composition may be prepared as pills, tablets, capsules, liquid medicine, etc.

Hereinafter, the present invention will be described in detail with reference to the attached drawings and experiment examples. However, the present invention is not limited thereto.

Figure 1:
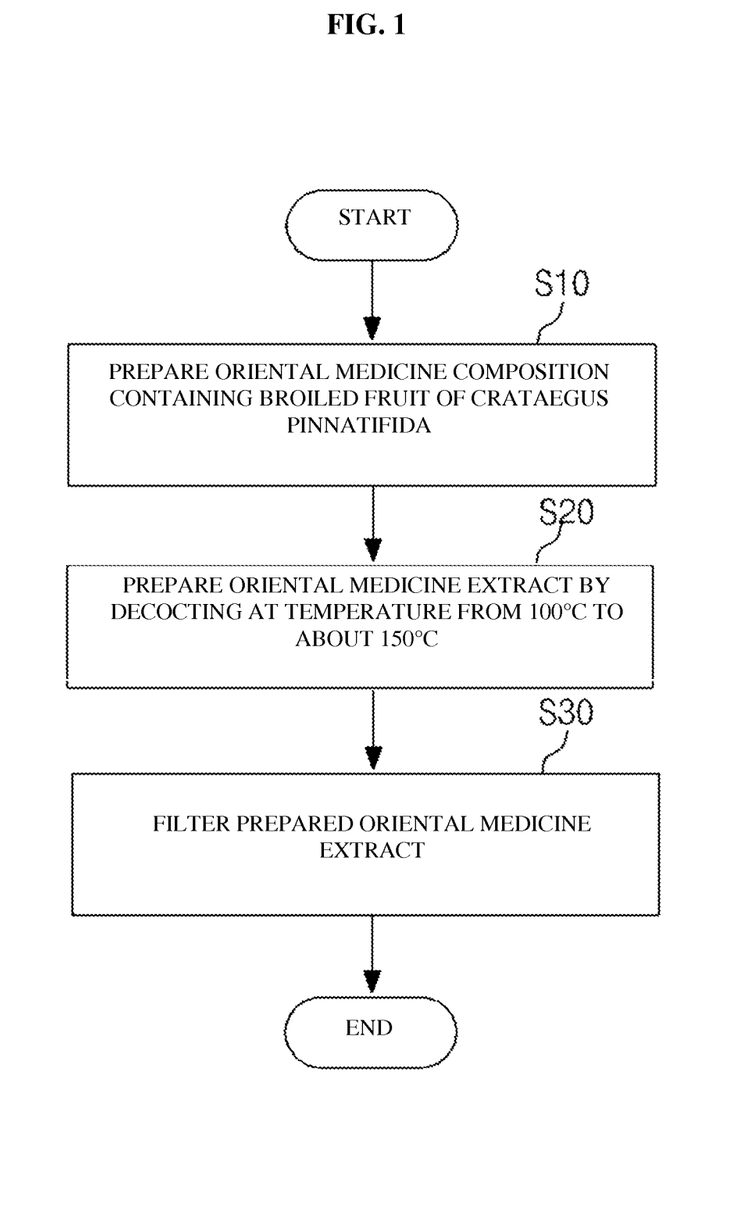
FIG. 1 is a flowchart showing a method of preparing an oriental medicine extract according to the first embodiment of the present invention or the second embodiment of the present invention.

FIG. 1 is a flowchart showing a method of preparing an oriental medicine extract according to the first embodiment of the present invention or the second embodiment of the present invention.

A method of preparing an oriental medicine extract from an oriental medicine composition according to an embodiment of the present invention will be described below. The oriental medicine composition containing from about 22 weight % to about 26 weight % of the broiled fruit of *Crataegus pinnatifida*, from about 17 weight % to about 21 weight % of the broiled root of *Atractylodes japonica*, from about 12 weight % to about 16 weight % of the dried peel of *Citrus unshiu*, from about 12 weight % to about 16 weight % of the broiled sprout of *Hordeum vulgare*, from about 7 weight % to about 11 weight % of the broiled fruit of *Amomum xanthioides* from about 5 weight % to about 9 weight % of the root of *Zingiber officinale*, from about 5 weight % to about 9 weight % of the dried fruit of *Zizyphi*, and from about 1 weight % to about 5 weight % of the horn of *Cervus elaphus* is prepared (operation S10). The oriental medicine composition may be a combination of general dried medicinal herbs, may be in the form of powders prepared by crushing the combination of the medicinal herbs, and may be a dried extraction material powders prepared by lyophilizing a hot water extraction material.

An oriental medicine extract may be obtained by decocting the prepared oriental medicine composition using water in a clay port at a temperature from about 100° C. to about 150° C. for a time period from about an hour and 20 minutes to about 2 hours and 20 minutes (operation S20). If the oriental medicine composition is decocted at a temperature lower than 100° C., effective ingredients may not be sufficiently extracted from the oriental medicine composition. Meanwhile, if the oriental medicine composition is decocted at a temperature higher than 150° C., effective ingredients extracted from the oriental medicine composition may be destroyed. Therefore, the oriental medicine composition may be decocted at a temperature from about 100° C. to about 150° C. Furthermore, if the oriental medicine composition is decocted for less than an hour and 20 minutes, effective ingredients may not be sufficiently extracted from the oriental medicine composition. Meanwhile, if the oriental medicine composition is decocted for more than 2 hours and 20 minutes, the effective ingredients are no longer extracted and an amount of the effective ingredients destroyed by high heat increases. Therefore, the oriental medicine composition may be decocted for a time period from about an hour and 20 minutes to about 2 hours and 20 minutes. An amount of water used for decocting the oriental medicine composition may be from about two to about five times larger than the overall amount of the oriental medicine composition.

The oriental medicine extract contains medicinal herb extraction materials at the same composition ratio as that of the medicinal herbs contained in the oriental medicine composition. Preferably, the oriental medicine extract may contain extraction materials of the broiled fruit of *Crataegus pinnatifida*, the broiled root of *Atractylodes japonica*, the dried peel of *Citrus unshiu*, the broiled sprout of *Hordeum vulgare*, the broiled fruit of *Amomum xanthioides*, the root of *Zingiber officinale*, the dried fruit of *Zizyphi*, and the horn of *Cervus elaphus* at ratios of 22~26:18~21:14~16:14~16: 9~11:6~8:6~8:1~4, with respect to the overall weight of the oriental medicine extract.

Alternatively, according to a method of preparing an oriental medicine extract from an oriental medicine composition according to the second embodiment of the present invention, An oriental medicine composition containing broiled fruit of *Crataegus pinnatifida*, broiled root of *Atractylodes japonica, Lufa cylidrica, Menthae Herba, Schizonepetae Spica*, dried peel of *Citrus unshiu*, broiled sprout of *Hordeum vulgare*, broiled fruit of *Amomum xanthioides, Astragali Radix*, root of *Zingiber officinale*, dried fruit of *Zizyphi*, and horn of *Cervus elaphus*, and preferably, may contain from about 13 weight % to about 17 weight % of the *Ulmi Cortex*, from about 10 weight % to about 15 weight % of the broiled fruit of *Crataegus pinnatifida*, from about 8 weight % to about 12 weight % of the broiled root of *Atractylodes japonica*, from about 8 weight % to about 12 weight % of the *Lufa cylidrica*, from about 8 weight % to about 12 weight % of the *Menthae Herba*, from about 5 weight % to about 10 weight % of the *Schizonepetae Spica*, from about 5 weight % to about 10 weight % of the dried peel of *Citrus unshiu*, from about 5 weight % to about 10 weight % of the broiled sprout of *Hordeum vulgare*, from about 3 weight % to about 7 weight % of the broiled fruit of *Amomum xanthioides*, from about 3 weight % to about 7 weight % of the *Astragali Radix*, from about 1 weight % to about 5 weight % of the root of *Zingiber officinale*, from about 1 weight % to about 5 weight % of the dried fruit of *Zizyphi*, and from about 0.5 weight % to about 3 weight % of the horn of *Cervus elaphus*, with respect to the overall weight of the oriental medicine composition is prepared first (operation S10). As described above, the oriental medicine composition may be a combination of general dried medicinal herbs, may be in the form of powders prepared by crushing the combination of the medicinal herbs, and may be a dried extraction material powders prepared by lyophilizing a hot water extraction material.

An oriental medicine extract may be obtained by decocting the prepared oriental medicine composition using water in a clay port at a temperature from about 100° C. to about 150° C. for a time period from about an hour and 20 minutes to about 2 hours and 20 minutes (operation S20). If the oriental medicine composition is decocted at a temperature lower than 100° C., effective ingredients may not be sufficiently extracted from the oriental medicine composition. Meanwhile, if the oriental medicine composition is decocted at a temperature higher than 150° C., effective ingredients extracted from the oriental medicine composition may be destroyed. Therefore, the oriental medicine composition may be decocted at a temperature from about 100° C. to about 150° C. Furthermore, if the oriental medicine composition is decocted for less than an hour and 20 minutes, effective ingredients may not be sufficiently extracted from the oriental medicine composition. Meanwhile, if the oriental medicine composition is decocted for more than 2 hours and 20 minutes, the effective ingredients are no longer extracted and an amount of the effective ingredients destroyed by high heat increases. Therefore, the oriental medicine composition may be decocted for a time period from about an hour and 20 minutes to about 2 hours and 20 minutes. An amount of water used for decocting the oriental medicine composition may be from about two to about five times larger than the overall amount of the oriental medicine composition.

The oriental medicine extract contains medicinal herb extraction materials at the same composition ratio as that of the medicinal herbs contained in the oriental medicine composition. Preferably, the oriental medicine extract may contain extraction materials of the broiled fruit of *Crataegus pinnatifida*, the broiled root of *Atractylodes japonica*, the dried peel of *Citrus unshiu*, the broiled sprout of *Hordeum vulgare*, the broiled fruit of *Amomum xanthioides*, the root of *Zingiber officinale*, the dried fruit of *Zizyphi*, and the horn of *Cervus elaphus* at ratios of 14~16:12~15:8~12:8~12: 8~12:6~8.5:6~8.5:6~8.5:4~6:4~6:3~5:3~5:0.5~2, with respect to the overall weight of the oriental medicine extract.

Next, the oriental medicine extract prepared from the oriental medicine composition according to the first embodiment of the present invention or the second embodiment of the present invention may be filtered and/or masked. When decoction of the oriental medicine composition is completed, the oriental medicine composition in a non-woven fabric bag may be taken out and removed, and the oriental medicine extract may be filtered by using a 150 mesh filter (operation S30). Furthermore, according to embodiments of the present invention, depressurization-condensation may be selectively performed after the filtering and masking operation. The oriental medicine extract filtered in the filtering and masking operation may be condensed to from about 10% to about 30% by using a depressurization-condenser.

According to embodiments of the present invention, any one or more from among fructose; sugars including unrefined sugar, refined sugar, turbinado, and dark brown sugar; natural sweeteners; synthetic sweeteners; maltitol syrup; polyglycitol syrup; palatinos; and oligosaccharides including malto-olygosaccharide, isomalto-olygosaccharide, and fracto-olygosaccharide may be added to the filtered/masked oriental medicine extract or the depressurization-condensed oriental medicine extract.

The fructose may be crystalline fructose or high fructose corn syrup, whereas the natural sweeteners may include at least one from among xylitol, erythritol, enzymatically modified stevia glucosyl stevia, stevioside, tomatine, thaumatin, thaumatin, monellin, glycyrrhizin, honey, Maple syrup, Agave syrup, and coconut sugar. The synthetic sweeteners may include at least one or more from among Aspartame, saccharin, acesulfame potassium, and Sucralose.

Any one or more from among the fructose, the sugars, the natural sweeteners, the synthetic sweeteners, the maltitol syrup, the polyglycitol syrup, the palatines, and the oligosaccharides may be additionally added at a composition ratio of from about 1 weight % to about 20 weight % with respect to the overall weight of the oriental medicine extract, where they may be added before or after the operation for filtering and masking the oriental medicine extract, the operation for depressurization-condensing the oriental medicine extract, or the operation for decocting the oriental medicine composition.

Furthermore, the oriental medicine composition may further contain various nutritional supplements, vitamins, minerals (electrolytes), flavoring agents, such as synthetic flavoring agents and natural flavoring agents, coloring agents and enhancers (cheese, chocolates, etc.), pectics acid and salts thereof, alginic acids and salts thereof, organic acids, protective colloid thickening agents, pH controlling adjusters, stabilizers, preservatives, glycerin, alcohols, and carbonizing agents use for carbonated beverages. Furthermore, the oriental medicine extract according to the present invention may contain natural fruit juices and fruit fleshes for preparing fruit juice beverages and vegetable beverages. The ingredients as described above may be used independently or in combination with one another. Although composition ratio of the additives is not important, the composition ratio of the additives with respect to the overall weight of an oriental medicine extract according to the present invention is generally selected within a range from about 0.001 weight % to about 20 weight %.

Hereinafter, embodiments of the present invention will be described in closer detail with reference to experimental examples. However, the experimental examples stated below are merely examples of the present invention, and the present invention is not limited thereto. Furthermore, the oriental medicine composition according to the embodiments of the present invention may be included in various health functional foods and health supplement foods having the above effects (particularly, for improving at least one of digestive functions and respiratory functions).

Experimental Example 1

From among 817 children in 81 daycare centers in Seoul and child patients in one oriental clinic in Seoul selected from Jul. 1, 2011 to Apr. 30, 2013, 108 children who satisfy conditions including being from 2 to 5 years old, not having chronic rhinitis, catching colds less than or equal to 4 times per year, having body mass index (BMI) equal to or greater than 15% and less than 25%, having been loss of appetite for 6 months or longer, and having estimated energy requirement (EER) less than −1S.D. or having BMI less than 15% and 108 guardians who are in charge of caring the 108 children were selected as an experimental group.

Next, an oriental medicine composition according to the composition ratio and dosages shown in Table 1 (referred to hereinafter as "SEC-22", that is, Sansa Extract Composition-22) was prepared and an oriental medicine extract was prepared based on the reference dosages according to body weights as shown in Table 2 below by decocting the oriental medicine composition using water of 120° C. temperature in a clay port for about 2 hours, where the children in the experimental group were instructed to take half or one-third of 120 cc of the oriental medicine extract two or three times per day.

TABLE 1

| Name of Medicine | Dosage(g)/Day/15 Kg |
| --- | --- |
| broiled fruit of Crataegus pinnatifida | 4.67 |
| broiled root of Atractylodes japonica | 3.73 |
| dried peel of Citrus unshiu | 2.80 |
| broiled sprout of Hordeum vulgare | 2.80 |
| broiled fruit of Amomum xanthioides | 1.87 |
| root of Zingiber officinale | 1.40 |
| dried fruit of Zizyphi | 1.40 |

TABLE 1-continued

| Name of Medicine | Dosage(g)/Day/15 Kg |
| --- | --- |
| horn of Cervus elaphus | 0.47 |
| crystalline fructose(Crystalline fructose) | 12.00 |

TABLE 2

| Measured Body Weight (Kg) | Reference Body Weight (Kg) |
| --- | --- |
| 7.6~10.5 | 9 |
| 10.6~13.5 | 12 |
| 13.6~16.5 | 15 |
| 16.6~19.5 | 18 |
| 19.6~22.5 | 21 |
| 22.6~25.5 | 24 |

The oriental medicine extract prepared from the SEC-22 contains medicinal herb extraction materials at the same composition ratio as that of the medicinal herbs contained in the SEC-22. Preferably, the oriental medicine extract may contain extraction materials of the broiled fruit of *Crataegus pinnatifida*, the broiled root of *Atractylodes japonica*, the dried peel of *Citrus unshiu*, the broiled sprout of *Hordeum vulgare*, the broiled fruit of *Amomum xanthioides*, the root of *Zingiber officinale*, the dried fruit of *Zizyphi*, and the horn of *Cervus elaphus* at ratios of 22~26:18~21:14~16:14~16:9~11:6~8:6~8:1~4, with respect to the overall weight of the oriental medicine extract excluding crystalline fructose.

Meanwhile, children in a comparison group were instructed to take half or one-third of 120 cc of placebo two or three times per day, which is prepared to have the same calories as that of SEC-22 and has the composition as shown in Table 3 below, two or three times per day.

TABLE 3

| Ingredients | Dosage(g)/Day/15 Kg |
| --- | --- |
| Molasses | 2.40 |
| Citric Acid | 0.16 |
| Trisodium Citrate | 0.04 |
| Herb Flavor | 0.36 |
| Crystalline Fructose | 12.0 + 1.8* |

*May be adjusted based on the reference dosages according to body weights as shown in Table 2 above Body measurements (height and weight), surveys (digestive symptom survey (Alarcon et al. 2003) and complex eating behavior survey), and dietary intake inquiries were performed with respect to the children the experimental group who have taken the SEC-22 and the children in the comparison group who have taken the placebo at their initial visits, after one month of treatment, after two months of treatment, after one month of observation after the treatment, and after two months of observation after the treatment.

Heights and weights of the children were measured with one decimal point while the children were wearing underwear only, BMI were calculated based on the heights and the weights, and BMI percentages were calculated by using the function in 2007 Korean National Growth Chart. From among digestive symptoms, average weekly frequencies for nausea, bloated stomach, stomachache, burp, and farts were recorded to confirm whether there were any discomforts in their gastrointestinal tracts.

Via the complex eating behavior survey, appetites, eating times, and complex eating habits were investigated, where the appetites were recorded in 7-point visual analog scale (VAS), and the eating times were recorded in minutes. The complex eating behavior survey included total 9 evaluation questions. After each equation was evaluated in 7-point VAS, points corresponding to those children with less complex eating habits were adjusted to 1 each and points corresponding to those children with more complex eating habits were adjusted to 7 each, and then the total points of 9 questions was calculated based on the adjusted points. Points for eating amounts were calculated by adding points for under-eating frequencies and frequencies of trying to feed to the points for the appetites, where the minimum of the points for eating amounts was 3 points and the maximum thereof was 21 points. Points for food neophobia were calculated by summing points for food neophobia (trial) and points for food neophobia (eager), where the minimum of the points for food neophobia was 2 points and the maximum thereof was 14 points The dietary intake survey was performed by instructing guardians who are in charge of caring children during their initial visit to record dietary intakes for 3 non-continuous days (two weekdays and one weekend day) while the children are without any diseases like colds and analyzing energy, the three major nutrients (carbohydrates, proteins, fats), and food groups by using the diet evaluation system (DES; DES-Korea Co., Seoul, Korea). To total energy intake ratios were calculated by applying 4 kcal/g for carbohydrates, 4 kcal/g for proteins, and 9 kcal/g for fats by using the Atwater factors.

As a result, as shown in Table 4 below, from among factors affecting complex eating behaviors, the complex eating habits of the children in the experimental group who have taken the SEC-22 were significantly enhanced as compared to the children in the comparison group who have taken the placebo. From among the complex eating habits, the frequencies of trying to feed of the children in the experimental group were significantly increased as compared to the children in the comparison group. Furthermore, the eating problems and the appetites of the children in the experimental group were significantly enhanced, and the total points for the complex eating habits of the children in the experimental group were significantly reduced as compared to the points at their initial visits.

TABLE 4

|  | Treatment Period | | | | Observation Period | | | |
| --- | --- | --- | --- | --- | --- | --- | --- | --- |
|  | One Month | | Two Months | | One Month | | Two Months | |
|  | Experimental Group | dried fruit of Zizyphi Group | Experimental Group | dried fruit of Zizyphi Group | Experimental Group | dried fruit of Zizyphi Group | Experimental Group | dried fruit of Zizyphi Group |
| Eating Time (min, %) | −1.9 ± 12 | −5.1 ± 12 | −6.2 ± 11 | −3.9 ± 10.8 | −6.7 ± 13 | −4.6 ± 12 | −6.1 ± 13.3 | −1.9 ± 12 |
| Eating Problem | −0.5 ± 1.3 | −0.4 ± 1.4 | −0.9 ± 2.0 | −0.4 ± 1.2 | −1.1 ± 1.9 | −0.7 ± 1.5 | −1.0 ± 1.7 | −0.6 ± 1.5 |
| Frequency of trying to eat | −0.4 ± 1.8 | −0.2 ± 1.1 | −0.9 ± 1.5 | −0.5 ± 1.4 | −1.2 ± 1.6 | −0.4 ± 1.4 | −1.2 ± 1.6 | −0.4 ± 1.7 |
| Appetite | 0.3 ± 1.2 | 0.6 ± 1.1 | 0.4 ± 1.3 | 0.4 ± 1.2 | 0.7 ± 1.3 | 0.7 ± 1.2 | 0.6 ± 1.1 | 0.4 ± 1.2 |

From among factors affecting dietary intakes, energy intakes, carbohydrates intakes, grain group intakes, and vegetable intakes of the children in the experimental group were significantly increased as compared to the children in the comparison group, and age-weight percentages of the children in the experimental group were significantly increased after one month of treatment, after two months of treatment, and after two months of observation as compared to those at their initial visits.

TABLE 5

|  | Treatment Period | | | | Observation Period | | | |
| --- | --- | --- | --- | --- | --- | --- | --- | --- |
|  | One Month | | Two Months | | One Month | | Two Months | |
|  | Experimental Group | dried fruit of Zizyphi Group | Experimental Group | Experimental Group | dried fruit of Zizyphi Group | Experimental Group | Experimental Group | dried fruit of Zizyphi Group |
| Energy (kcal/day) | 131 ± 390 | 23 ± 204 | 116 ± 307 | 91 ± 300 | 87 ± 326 | 59 ± 235 | 137 ± 380 | 6 ± 296 |
| Carbohydrate (% Energy) | 0.6 ± 6.3 | 1.2 ± 6.9 | 0.4 ± 5.8 | 1.2 ± 7.0 | 0.9 ± 5.8 | 2.3 ± 6.2 | 1.9 ± 6.4 | 0.9 ± 7.3 |
| Increase of Grain Group Intake Compared to the Initial visit (%) | 0.2 ± 0.6 | 0.2 ± 3.3 | 0.3 ± 0.6 | 0.3 ± 0.5 | 0.2 ± 0.6 | 0.2 ± 0.5 | 0.1 ± 1.4 | 0.0 ± 1.4 |

TABLE 5-continued

| | Treatment Period | | | | Observation Period | | | |
|---|---|---|---|---|---|---|---|---|
| | One Month | | | | | | One Month | |
| | | dried fruit of Zizyphi Group | Two Months | | dried fruit of Zizyphi Group | | | dried fruit of Zizyphi Group |
| | Experimental Group | | Experimental Group | Experimental Group | | Experimental Group | Experimental Group | |
| Increase of Vegetable Group Intake Compared to the Initial visit (%) | 0.3 ± 1.4 | −0.1 ± 2 | 0.5 ± 1.2 | 0.1 ± 1.9 | 0.4 ± 1.3 | 0.2 ± 0.6 | 1.0 ± 1.9 | 0.3 ± 2.4 |

As shown in Table 5 above, the energy intakes significantly increased only in the experimental group. Particularly, it seems that the significant increases in the carbohydrates intakes were led to increases in the energy intakes. Furthermore, in the food groups, the grain group intakes increased, where the main reason of the increased energy intakes was increases of rice intakes, because Koreans live on rice.

Figure 2:
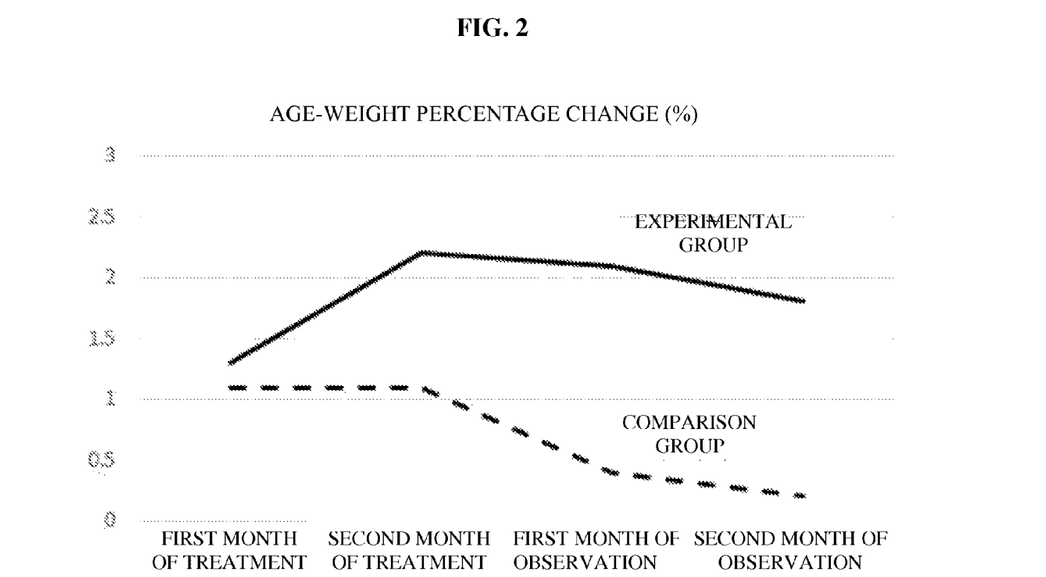
FIG. 2 is a graph showing changes of age-weight percentages based on taking an oriental medicine extract prepared from an oriental medicine composition according to an embodiment of the present invention.
Figure 3:
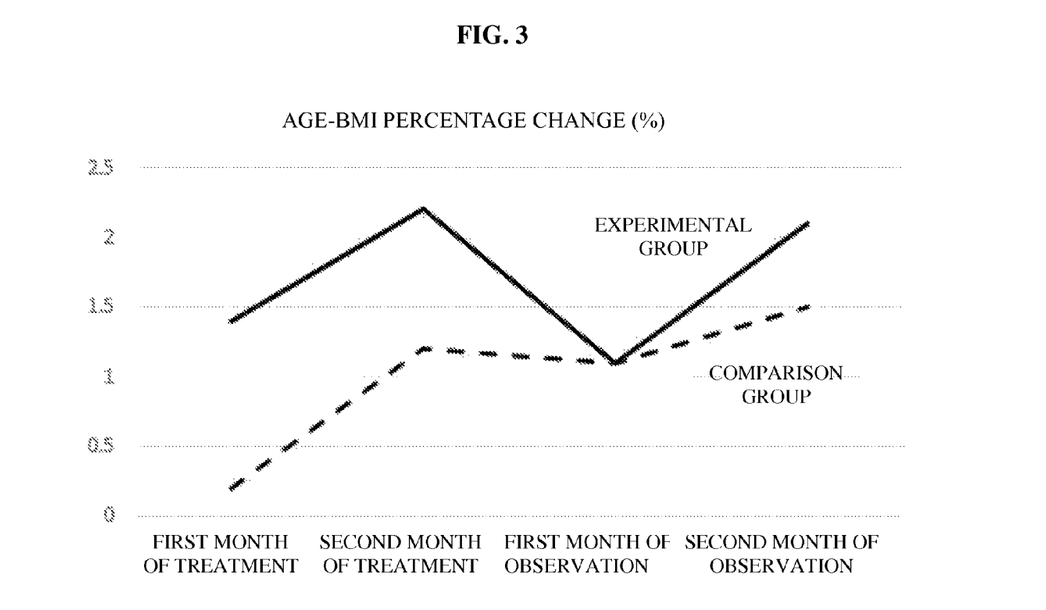
FIG. 3 is a graph showing changes of body mass index (BMI) percentages based on taking an oriental medicine extract prepared from an oriental medicine composition according to an embodiment of the present invention.

Furthermore, FIGS. 2 and 3 are graphs showing changes of age-weight percentages and BMIs of the children in the experimental group who have taken the SEC-22 and the children in the comparison group who have taken the placebo, as compared to those at their initial visits. Referring to FIGS. 2 and 3 and Table 6 below, although age-height percentages of the children in the experimental group and the comparison group were not significantly changed from their initial visits, age-weight percentages of only the children in the experimental group were significantly increased after one month of treatment and after two months of treatment from those of their initial visits and were also significantly increased after two months of observation. Furthermore, BMI percentages of only the children in the experimental group were significantly increased after two months of treatment and after two months of observation from those of their initial visits. The results shown in Table 6 below were calculated based on age-height percentages, age-weight percentages, and BMIs of the children at their initial visits.

visits. Therefore, the SEC-22 may help even non-underweighted children having skinny proportions for increasing appetites, energy and nutrients intakes, BMI percentages, and weights.

Experimental Example 2

From among 817 children in 81 daycare centers in Seoul and child patients in one oriental clinic in Seoul selected from Jul. 1, 2011 to Apr. 30, 2013, 86 children who satisfy conditions including being from 2 to 5 years old, not having chronic rhinitis, catching colds more than 4 times per year, having body mass index (BMI) from about 15% and to about 25%, having been loss of appetite for 6 months or longer, and having estimated energy requirement (EER) less than −1 S.D. or having BMI less than 15% in 3-day dietary survey and 86 guardians who are in charge of caring the 86 children were selected as an experimental group. Here, the chronic rhinitis refers to cases where symptoms including sneeze, runny nose, nasal congestion, uredo, and postnasal drip persist continuously or non-continuously for 12 weeks or longer during a year (except rhinitis based on abnormality in intranasal structure or drug-induced rhinitis).

Next, an oriental medicine composition according to the composition ratio and dosages shown in Table 7 (referred to hereinafter as "SEC-33", that is, Sansa Extract Composition-33) was prepared and an oriental medicine extract was

TABLE 6

| | Treatment Period | | | | Observation Period | | | |
|---|---|---|---|---|---|---|---|---|
| | One Month | | | | | | One Month | |
| | | dried fruit of Zizyphi Group | Two Months | | dried fruit of Zizyphi Group | | | dried fruit of Zizyphi Group |
| | Experimental Group | | Experimental Group | Experimental Group | | Experimental Group | Experimental Group | |
| Age-Height percentage (%) | −1.4 ± 4.5 | −1.3 ± 8.8 | −0.8 ± 5.7 | −0.4 ± 5.5 | −0.1 ± 6.0 | −0.6 ± 6.1 | −0.9 ± 5.5 | −0.3 ± 6.9 |
| Age-Weight percentage (%) | 1.3 ± 3.5 | 1.1 ± 5.4 | 2.2 ± 3.8 | 1.1 ± 4.7 | 2.1 ± 7.5 | 0.4 ± 5.5 | 1.8 ± 4.1 | 0.2 ± 5.6 |
| BMI(%) | 1.4 ± 5.2 | 0.2 ± 4.3 | 2.2 ± 5.6 | 1.2 ± 4.6 | 1.1 ± 5.3 | 1.1 ± 6.5 | 2.1 ± 5.1 | 1.5 ± 8.0 |

As described above, as children having skinny proportions have taken oriental medicine extract prepared from the SEC-22, complex eating habits (particularly, eating amounts) were enhanced with improved appetites, energy intakes (particularly, carbohydrates) intakes increased, and age-weight percentages and BMI percentages were also significantly increased as compared to those at their initial prepared based on the reference dosages according to body weights as shown in Table 2 below by decocting the oriental medicine composition using water of 120° C. temperature in a clay port for about 2 hours, where the children in the experimental group were instructed to take half or one-third of 120 cc of the oriental medicine extract two or three times per day.

TABLE 7

| Ingredients | Dosage(g)/Day/15 Kg |
|---|---|
| Ulmi Cortex | 5.60 |
| broiled fruit of Crataegus pinnatifida | 4.67 |
| broiled root of Atractylodes japonica | 3.73 |
| Lufa Cylidrica | 3.73 |
| Menthae Herba | 3.73 |
| Schizonepetae Spica | 2.80 |
| dried peel of Citrus unshiu | 2.80 |
| broiled sprout of Hordeum vulgare | 2.80 |
| broiled fruit of Amomum xanthioides | 1.87 |
| Astragali Radix | 1.87 |
| root of Zingiber officinale | 1.40 |
| dried fruit of Zizyphi | 1.40 |
| horn of Cervus elaphus | 0.47 |
| Crystalline fructose | 12.00 |

Meanwhile, children in a comparison group were instructed to take half or one-third of 120 cc of a placebo, which is prepared to have the same calories as that of SEC-33 and has the composition as shown in Table 8 below, two or three times per day.

The oriental medicine extract prepared from the SEC-33 contains medicinal herb extraction materials at the same composition ratio as that of the medicinal herbs contained in the SEC-33. Preferably, the oriental medicine extract may contain extraction materials of the *Ulmi Cortex*, the broiled fruit of *Crataegus pinnatifida*, the broiled root of *Atractylodes japonica, Lua cylindrica*, the dried peel of *Citrus unshiu*, the broiled sprout of *Hordeum vulgare*, the broiled fruit of *Amomum xanthioides*, the *Astragali Radix*, the root of *Zingiber officinale*, the dried fruit of *Zizyphi*, and the horn of *Cervus elaphus* at ratios of 14~16:12~15:8~12:8~12:8~12:6~8.5:6~8.5:6~8.5:4~6:4~6:3~5:3~5:0.5~2, with respect to the overall weight of the oriental medicine extract excluding crystalline fructose.

TABLE 8

| Ingredients | Dosage(g)/Day/15 Kg |
|---|---|
| Molasses | 2.40 |
| Citric Acid | 0.16 |
| Trisodium Citrate | 0.04 |
| Herb Flavor | 0.36 |
| Crystalline Fructose | 12.0 + 13.0* |

*May be adjusted based on the reference dosages according to body weights as shown in Table 2 above.

Body measurements (height and weight), surveys (digestive symptom survey (Alarcon et al. 2003) and complex eating behavior survey), and dietary intake inquiries were performed with respect to the children in the experimental group and the comparison group, who have respectively taken the SEC-33 and the placebo, at their initial visits, after one month of treatment, after two months of treatment, after one month of observation after the treatment, and after two months of observation after the treatment. The body measurements, the surveys, and the dietary intake inquiries were performed in the same manner as in the Experimental Example 1.

As a result, from among factors affecting complex eating behaviors, eating times and the complex eating habits including the eating problems, the appetites, and the frequencies of trying to feed of the children in the experimental group were significantly increased as compared to the children in the comparison group, and the total points for the complex eating habits of the children in the experimental group were significantly reduced as compared to the points at their initial visits.

TABLE 9

| | Treatment Period | | | | Observation Period | | | |
|---|---|---|---|---|---|---|---|---|
| | One Month | | Two Months | | One Month | | | |
| | Experimental Group | dried fruit of Zizyphi Group | Experimental Group | Experimental Group | dried fruit of Zizyphi Group | Experimental Group | Experimental Group | dried fruit of Zizyphi Group |
| Eating Time (min, %) | −5.5 ± 10.6 | −4.1 ± 9.1 | −6.5 ± 13.9 | −3.6 ± 13.1 | −6.0 ± 12.8 | −5.5 ± 11.7 | −6.2 ± 14.2 | −3.6 ± 13.8 |
| Eating Problem | −0.3 ± 1.3 | −0.2 ± 1.3 | −0.6 ± 1.5 | 0.0 ± 1.5 | −0.8 ± 1.6 | −0.6 ± 1.8 | −0.9 ± 1.7 | −0.4 ± 1.5 |
| Frequency of trying to eat | −0.5 ± 1.5 | −0.1 ± 1.7 | −0.6 ± 1.2 | 0.0 ± 1.9 | −0.8 ± 1.3 | −0.3 ± 2.0 | −1.0 ± 1.5 | 0.2 ± 2.0 |
| Appetite | 0.2 ± 1.0 | −0.1 ± 1.4 | 0.5 ± 1.2 | 0.0 ± 1.5 | 0.4 ± 1.0 | 0.3 ± 1.3 | 0.6 ± 1.3 | 0.4 ± 1.4 |

Figure 4:
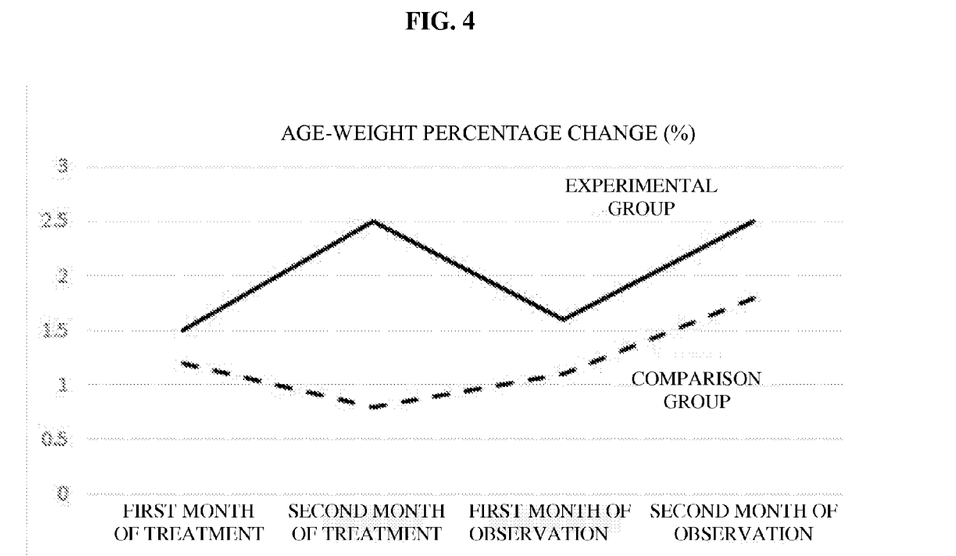
FIG. 4 is a graph showing changes of age-weight percentages based on taking an oriental medicine extract prepared from an oriental medicine composition according to another embodiment of the present invention.
Figure 5:
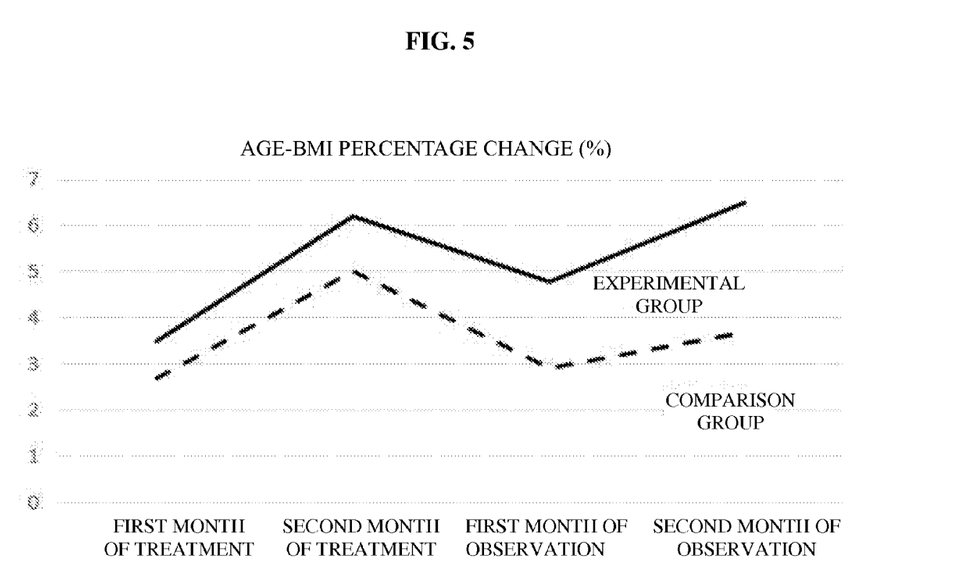
FIG. 5 is a graph showing changes of body mass index (BMI) percentages based on taking an oriental medicine extract prepared from an oriental medicine composition according to another embodiment of the present invention.

Furthermore, a result of analyzing effects on growths is as described below. FIGS. 4 and 5 are graphs showing changes of age-weight percentages and BMIs of the children in the experimental group who have taken the SEC-33 and the children in the comparison group who have taken the placebo, as compared to those at their initial visits, and Table 10 shows changes of age-weight percentages and BMIs of the children in the experimental group who have taken the SEC-33 and the children in the comparison group who have taken the placebo after one and two months of treatment and after one and two months of observation, as compared to those at their initial visits Referring to Table 10 and FIGS. 4 and 5, age-weight percentages of the children in both the experimental group and the comparison group were significantly increased after two months of treatment from those of their initial visits, where the increases corresponding to the children in the experimental group were relatively large as compared to the increases corresponding to the children in the comparison group. BMI percentages of the children in both the experimental group and the comparison group were significantly increased after one and two months of treatment and after one and two months of observation from those of their initial visits.

According to another embodiment of the present invention, an oriental medicine composition contains not only broiled fruit of *Crataegus pinnatifida*, broiled root of *Atractylodes japonica*, dried peel of *Citrus unshiu*, broiled sprout of *Hordeum vulgare*, broiled fruit of *Amomum xanthioides*, root of *Zingiber officinale*, dried fruit of *Zizyphi*, and horn of *Cervus elaphus*, but also *Ulmi Cortex*, *Lufa cylindrica*, *Menthae Herba*, *Schizonepetae Spica*, and *Astragali Radix*. Therefore, the oriental medicine composition may improve not only digestive functions, but also respiratory functions, thereby promoting growths of children having skinny proportions and improving underweight.

According to another embodiment of the present invention, an oriental medicine extract for improving health of underweighted children by increasing weight, strengthening immune system, improving stamina, and promoting growth by enhancing not only digestive functions, but also respiratory functions may be provided by extracting the oriental medicine extract by decocting the oriental medicine composition and filtering the oriental medicine extract. Furthermore, the oriental medicine composition according to the embodiments of the present invention may be included in various health functional foods and health supplement foods

TABLE 11

| | Treatment Period | | | | Observation Period | | | |
|---|---|---|---|---|---|---|---|---|
| | One Month | | Two Months | | One Month | | | |
| | Experimental roup | dried fruit of Zizyphi Group | Experimental Group | Experimental Group | dried fruit of Zizyphi Group | Experimental Group | Experimental Group | dried fruit of Zizyphi Group |
| Age-Weight percentage (%) | 1.5 ± 5.3 | 1.2 ± 5.5 | 2.5 ± 5.7 | 0.8 ± 6.3 | 1.6 ± 6.9 | 1.1 ± 6.5 | 2.5 ± 6.5 | 1.8 ± 6.5 |
| BMI (%) | 2.7 ± 5.2 | 0.8 ± 4.6 | 5.0 ± 7.9 | 1.2 ± 6.8 | 2.9 ± 7.3 | 1.9 ± 7.0 | 3.7 ± 8.4 | 2.8 ± 9.8 |

As described above, as children having skinny proportions have taken oriental medicine extract prepared from the SEC-33, complex eating habits (particularly, eating amounts) were enhanced with improved appetites, energy intakes (particularly, carbohydrates) intakes increased, and age-weight percentages and BMI percentages were also significantly increased as compared to those at their initial visits. Particularly, the increases in the age-weight percentages and the BMI percentages of the children in the experimental group were more significant that the increases in those of the children in the experimental group in the experimental example 1 who have taken an oriental medicine extract prepared from the SEC-22. Therefore, the SEC-33 and an oriental medicine extract prepared from the SEC-33 may help even non-underweighted children having skinny proportions for increasing appetites, energy and nutrients intakes, BMI percentages, and weights by improving respiratory diseases.

According to an embodiment of the present invention, an oriental medicine composition contains broiled fruit of *Crataegus pinnatifida*, broiled root of *Atractylodes japonica*, dried peel of *Citrus unshiu*, broiled sprout of *Hordeum vulgare*, broiled fruit of *Amomum xanthioides*, root of *Zingiber officinale*, dried fruit of *Zizyphi*, and horn of *Cervus elaphus*. Therefore, the oriental medicine composition may improve digestive functions and respiratory functions by increasing eating amounts of children with loss of appetites by enhancing digestive functions.

having the above effects (particularly, for improving at least one of digestive functions and respiratory functions).

While the present disclosure has been described with reference to the embodiments illustrated in the figures, the embodiments are merely examples, and it will be understood by those skilled in the art that various changes in form and other embodiments equivalent thereto can be performed. Therefore, the technical scope of the disclosure is defined by the technical idea of the appended claims.

The drawings and the forgoing description gave examples of the present invention. The scope of the present invention, however, is by no means limited by these specific examples. Numerous variations, whether explicitly given in the specification or not, such as differences in structure, dimension, and use of material, are possible. The scope of the invention is at least as broad as given by the following claims.

What is claimed is:

1. An oriental medicine composition for promoting growth in children by improving digestive and respiratory functions, the oriental medicine composition comprising:
   from about 22 weight % to about 26 weight % of the broiled fruit of *Crataegus pinnatifida*;
   from about 17 weight % to about 21 weight % of the broiled root of *Atractylodes japonica*;
   from about 12 weight % to about 16 weight % of the dried peel of *Citrus unshiu*;

from about 12 weight % to about 16 weight % of the broiled sprout of *Hordeum vulgare*;

from about 7 weight % to about 11 weight % of the broiled fruit of *Amomum xanthioides*;

from about 5 weight % to about 9 weight % of the root of *Zingiber officinale*;

from about 5 weight % to about 9 weight % of the dried fruit of *Zizyphi*; and from about 1 weight % to about 5 weight % of the horn of *Cervus elaphus*.

2. The oriental medicine composition of claim 1, further comprising at least one from among fructose; sugars including unrefined sugar, refined sugar, turbinado, and dark brown sugar; natural sweeteners; synthetic sweeteners; maltitol syrup; polyglycitol syrup; palatinos; and oligosaccharides including malto-olygosaccharide, isomalto-olygosaccharide, and fracto-olygosaccharide.

3. The oriental medicine composition of claim 1, wherein the fructose is crystalline fructose or high fructose corn syrup.

4. The oriental medicine composition of claim 2, wherein the natural sweeteners comprises at least one from among xylitol, erythritol, enzymatically modified stevia glucosyl stevia, stevioside, tomatine, thaumatin, thaumatin, monellin, glycyrrhizin, honey, Maple syrup, Agave syrup, and coconut sugar.

5. The oriental medicine composition of claim 2, wherein the synthetic sweeteners comprises at least one or more from among Aspartame, saccharin, acesulfame potassium, and Sucralose.

6. The oriental medicine composition of claim 1, wherein the broiled fruit of *Crataegus pinnatifida* is fruit of the hawthorn.

7. An oriental medicine composition for improving digestive functions and respiratory functions, the oriental medicine composition comprising:

from about 13 weight % to about 17 weight % of *Ulmi Cortex*;

from about 10 weight % to about 15 weight % of broiled fruit of *Crataegus pinnatifida*;

from about 8 weight % to about 12 weight % of broiled root of *Atractylodes japonica*;

from about 8 weight % to about 12 weight % of *Lufa cylidrica*;

from about 8 weight % to about 12 weight % of *Menthae Herba*;

from about 5 weight % to about 10 weight % of *Schizonepetae Spica*;

from about 5 weight % to about 10 weight % of dried peel of *Citrus unshiu*;

from about 5 weight % to about 10 weight % of broiled sprout of *Hordeum vulgare*;

from about 3 weight % to about 7 weight % of broiled fruit of *Amomum xanthioides*;

from about 3 weight % to about 7 weight % of *Astragali Radix*;

from about 1 weight % to about 5 weight % of root of *Zingiber officinale*;

from about 1 weight % to about 5 weight % of dried fruit of *Zizyphi*; and from about 0.5 weight % to about 3 weight % of horn of *Cervus elaphus*, with respect to the overall weight of the oriental medicine composition.

8. The oriental medicine composition of claim 7, further comprising at least one from among fructose comprising crystalline fructose and high fructose corn syrup; sugars comprising unrefined sugar, refined sugar, turbinado, and dark brown sugar; natural sweeteners comprising xylitol, erythritol, enzymatically modified stevia glucosyl stevia, stevioside, tomatine, thaumatin, thaumatin, monellin, glycyrrhizin, honey, Maple syrup, Agave syrup, and coconut sugar; synthetic sweeteners comprising Aspartame, saccharin, acesulfame potassium, and Sucralose; maltitol syrup; polyglycitol syrup; palatinos; and oligosaccharides comprising malto-olygosaccharide, isomalto-olygosaccharide, and fracto-olygosaccharide.

9. A method of preparing an oriental medicine extract for improving digestive functions and respiratory functions, the method comprising:

preparing an oriental medicine composition containing from about 22 weight % to about 26 weight % of the broiled fruit of *Crataegus pinnatifida*, from about 17 weight % to about 21 weight % of the broiled root of *Atractylodes japonica*, from about 12 weight % to about 16 weight % of the dried peel of *Citrus unshiu*, from about 12 weight % to about 16 weight % of the broiled sprout of *Hordeum vulgare*, from about 7 weight % to about 11 weight % of the broiled fruit of *Amomum xanthioides* from about 5 weight % to about 9 weight % of the root of *Zingiber officinale*, from about 5 weight % to about 9 weight % of the dried fruit of *Zizyphi*, and from about 1 weight % to about 5 weight % of the horn of *Cervus elaphus*;

putting the oriental medicine composition in a non-woven fabric bag, putting the non-woven fabric bag in a clay port accommodating water, and preparing the oriental medicine extract by decocting the oriental medicine composition; and filtering the oriental medicine extract.

10. The method of claim 9, further comprising, after the filtering of the oriental medicine extract, adding at least one from among fructose; sugars including unrefined sugar, refined sugar, turbinado, and dark brown sugar; natural sweeteners; synthetic sweeteners; maltitol syrup; polyglycitol syrup; palatinos; and oligosaccharides including malto-olygosaccharide, isomalto-olygosaccharide, and fracto-olygosaccharide to the filtered oriental medicine extract.

11. The method of claim 9, further comprising, after the filtering of the oriental medicine extract, depressurization-condensing the filtered oriental medicine extract.

12. The method of claim 11, wherein the fructose is crystalline fructose or high fructose corn syrup.

13. The method of claim 11, wherein the natural sweeteners comprises at least one from among xylitol, erythritol, enzymatically modified stevia glucosyl stevia, stevioside, tomatine, thaumatin, thaumatin, monellin, glycyrrhizin, honey, Maple syrup, Agave syrup, and coconut sugar, and the synthetic sweeteners comprises at least one or more from among Aspartame, saccharin, acesulfame potassium, and Sucralose.

14. The method of claim 13, further comprising, after the filtering of the oriental medicine extract, depressurization-condensing the filtered oriental medicine extract; and drying the oriental medicine extract and preparing the dried oriental medicine extract in the form of powders.

15. An oriental medicine extract for improving digestive functions and respiratory functions, the oriental medicine extract prepared according to claim 9.

* * * * *